(12) United States Patent
Engel et al.

(10) Patent No.: US 8,470,351 B2
(45) Date of Patent: Jun. 25, 2013

(54) EMBEDDING ANTIBIOTIC COMPOUNDS IN SOLID POLYMERS

(75) Inventors: Robert Engel, Carle Place, NY (US); JaimeLee Iolani Rizzo, Glen Cove, NY (US); Karin Melkonian Fincher, Garden City, NY (US); Gary Innocenti, Franklin Lakes, NJ (US)

(73) Assignees: The Research Foundation of the City University of New York, New York, NY (US); Pace University, New York, NY (US); Long Island University, Brookville, NY (US)

( * ) Notice: Subject to any disclaimer, the term of this patent is extended or adjusted under 35 U.S.C. 154(b) by 587 days.

(21) Appl. No.: 12/129,805

(22) Filed: May 30, 2008

(65) Prior Publication Data

US 2008/0300252 A1 Dec. 4, 2008

Related U.S. Application Data

(60) Provisional application No. 60/940,827, filed on May 30, 2007, provisional application No. 60/941,822, filed on Jun. 4, 2007.

(51) Int. Cl.
*A01N 25/34* (2006.01)

(52) U.S. Cl.
USPC ........... 424/402; 424/404; 424/405; 424/411; 514/252.11; 514/300; 524/87; 524/92; 524/601; 524/605

(58) Field of Classification Search
USPC ................ 524/92, 601, 605, 87, 97; 424/402, 424/411; 544/351; 514/252.11
See application file for complete search history.

(56) References Cited

U.S. PATENT DOCUMENTS

| | | | | |
|---|---|---|---|---|
| 4,097,431 | A * | 6/1978 | Asahara et al. | 524/120 |
| 4,891,391 | A * | 1/1990 | McEntee | 523/122 |
| 5,263,992 | A | 11/1993 | Guire | |
| 5,476,509 | A | 12/1995 | Keogh et al. | |
| 5,906,825 | A * | 5/1999 | Seabrook et al. | 424/404 |
| 6,033,719 | A | 3/2000 | Keogh | |
| 6,299,604 | B1 | 10/2001 | Ragheb et al. | |
| 6,306,454 | B1 | 10/2001 | Ung-Chhun et al. | |
| 6,436,419 | B1 | 8/2002 | Sun et al. | |
| 6,444,415 | B1 | 9/2002 | Tanaka et al. | |
| 7,285,286 | B2 | 10/2007 | Engel et al. | |
| 2002/0114769 | A1* | 8/2002 | Rotenberg et al. | 424/59 |
| 2005/0181006 | A1 | 8/2005 | Engel et al. | |
| 2006/0041123 | A1 | 2/2006 | Axten et al. | |
| 2006/0128850 | A1 | 6/2006 | Jariwala et al. | |
| 2010/0179156 | A1* | 7/2010 | Engel et al. | 514/249 |

FOREIGN PATENT DOCUMENTS

| | | |
|---|---|---|
| EP | 0514588 | 11/1997 |
| EP | 0 998 851 A1 | 5/2000 |
| GB | 2 404 920 A | 2/2005 |
| WO | WO00/15897 | 3/2000 |
| WO | WO2005016972 A1 | 2/2005 |
| WO | WO 2005021626 A2 | 3/2005 |

OTHER PUBLICATIONS

Cohen et al., "Polycations. 4. Synthesis and Antihydrophobic Effect of Polycationic Strings", Tetrahedron Letters. 1998, pp. 8617-8620.*
Cohen et al., "Polycations. IX. Polyammonium derivatives of cyclodextrins: syntheses and binding to organic oxyanions;" Heteroatom Chemistry. 11:546-555, 2000.
Fabian et al., "Polycations: Syntheses of polyammonium strings as antibacterial agents;" SYNLETT. 1007-1009, Aug. 1997.
Strekas et al., "Polycations 5. Inducement of DNA circular dichroism signals for duplex deoxyribonucleotide homopolymers by polycationic strings;" Archives of Biochemistry and Biophysics. 364(1):129-131, 1999.
Kanazawa et al., "Polymeric phosphonium salts as a novel class of cationic biocides. III. Immobilization of phosphonium salts by surface photografting and antibacterial activity of the surface-treated polymer films;" Journal of Polymer Science. 31:1467-1472, 1993.
Tiller et al., "Designing surfaces that kill bacteria on contact;" PNAS. 98(11):5981-5985, May 22, 2001.
Isquith et al., "Surface-bonded antimicrobial activity of an organosilicon quaternary ammonium chloride;" Applied Microbiology. 24(6):859-863, Dec. 1972.
Krause, "A universal technique for antimicrobial surface preparation using quaternary ammonium-functionalized dendrimers;" http://es.eps.gov/ncer_abstracts/sbir/02/phase1/pollution/krause.html, Sep. 27, 2002.
Cohen et al., Letters in Drug Design & Discovery 2004, 1(1):88-90.

* cited by examiner

*Primary Examiner* — Nicole M Buie-Hatcher
(74) *Attorney, Agent, or Firm* — Hoffmann & Baron, LLP

(57) ABSTRACT

The present invention is directed to providing antimicrobial compositions consisting of a polymeric material and, embedded therein, an antimicrobial compound. The antimicrobial compound contains at least one quaternary ammonium group, at least one hydrocarbon chain comprising a minimum of 10 carbon atoms and a maximum of 24 carbon atoms, and one or more anions to balance the charge of the quaternary ammonium groups. The invention is also directed to a method of making antimicrobial compositions containing an antimicrobial compound embedded in a polymeric material.

28 Claims, No Drawings

EMBEDDING ANTIBIOTIC COMPOUNDS IN SOLID POLYMERS

CROSS-REFERENCE TO RELATED APPLICATIONS

This application claims the benefit of U.S. Provisional Application Ser. No. 60/940,827, filed May 30, 2007 and 60/941,822, filed Jun. 4, 2007, which are incorporated herein by reference.

BACKGROUND OF THE INVENTION

Current fears of antibiotic-resistant bacteria and other microbes as well as of bioterrorism have increased the importance of developing new ways to protect people from microbial infection. It is, for example, important to develop new solid compositions that provide antimicrobial protection without creating antibacterial resistant microbes. Such compositions would be useful, for example, in hospitals and during military and civilian operations where bacterial contamination has occurred, or is expected to occur.

In developing new antimicrobial compositions, it is important to discourage further antibiotic resistance. Ideally, therefore, novel antimicrobial compositions will function through non-specific, non-metabolic mechanisms.

For example, polycationic (quaternary ammonium) strings were developed in the laboratory of Robert Engel. See Fabian et al, Syn. Lett., 1007 (1997); Strekas et al, Arch. Biochem. and Biophys. 364, 129-131 (1999). These strings are reported to have antibacterial activity. See Cohen et al, Heteroat. Chem. 11, 546-555 (2000).

It is known to coat antimicrobial agents on surfaces. The coating may, however, wash or wear-off, causing the surface to be unprotected from microbes.

There is, clearly, a need for improved new solid antimicrobial compositions and products that are more stable than those known heretofore. Ideally, the compositions and products do not lead to bacterial resistance, and are permanent over time.

SUMMARY OF THE INVENTION

The present invention relates to a solid antimicrobial composition including a polymeric material that is solid at room temperature and molten at elevated temperatures and, embedded therein, a compound including at least one quaternary ammonium group that contains at least one hydrocarbon chain with a minimum of 10 carbon atoms and a maximum of 24 carbon atoms, and one or more anions to balance the charge of the quaternary ammonium groups.

In a preferred embodiment, the polymeric material is selected from the group consisting of polyvinyl chloride, a polyester, polyethylene, polypropylene, polystyrene, polymethacrylate, polyacrylate, polyacrylamide, nylon, and rayon. The polyester is preferably polyethylene terephthalate or poly-1,4, cyclohexylenedimethylene terephthalate. The polymeric material is preferably natural or synthetic rubber.

The quaternary ammonium group is preferably

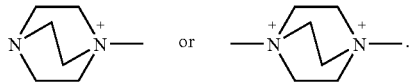

In a preferred embodiment, the solid antimicrobial composition is represented by formula (I):

$$R^1—Y^1—X—Z—(X—Y^2—R^2)_n aB^{-c} \qquad (I).$$

In formula (I), Z represents a modified polyol having more than one primary hydroxyl group in its unmodified state, wherein at least two of the primary hydroxyl groups have been replaced by $R^1—Y^1—X$ or $R^2—Y^2—X$ groups. X represents 1,4-diazoniabicyclo[2.2.2]octane. $Y^1$ and $Y^2$ independently represent hydrocarbon chains comprising a minimum of 10 carbon atoms and a maximum of 24 carbon atoms. $R^1$ and $R^2$ independently represent H, halo, or $OR^3$. $R^3$ represents H or $R^4$. $R^4$ represents $—C(O)R^5$ or $R^6$. $R^5$ represents H or a hydrocarbon group comprising a minimum of 1 carbon atom and a maximum of 4 carbon atoms. $R^6$ represents a hydrocarbon group comprising a minimum of 1 carbon atom and a maximum of 4 carbon atoms. The letter n represents a number up to m−1 wherein m represents the number of primary hydroxyl groups in the unmodified polyol. B represents an anion. The letter a represents an integer, and c represents 1-3, wherein a×c=2n+2.

In one preferred embodiment, the at least one quaternary ammonium group is part of a five or six member ring wherein the ring is unfused or is a fused ring system that contains one or two additional fused rings, and wherein the ring or fused ring system is unsubstituted or is substituted with one or more lower alkyl, halo, hydroxy, lower alkoxy, amino, lower alkylamino, or di-lower alkylamino group or nitro group. In another preferred embodiment, the quaternary ammonium group comprises a trimethylammonium group.

The invention also relates to a method of making a solid antimicrobial composition, the method including:

i) providing a polymeric material that is in a solid state at room temperature;

ii) melting the polymeric material at temperatures up to about 400° C. to form a molten polymeric material;

iii) adding an antimicrobial compound to the molten polymeric material to form a mixture of the compound embedded in the polymeric material, wherein the compound comprises at least one quaternary ammonium group, at least one hydrocarbon chain comprising a minimum of 10 carbon atoms and a maximum of 24 carbon atoms, and one or more anions to balance the charge of the quaternary ammonium groups; and iv) cooling the mixture until it solidifies.

Preferably, the polymeric material is heated at temperatures up to about 500° F. to form a molten polymeric material.

The invention also relates to a method of converting a polymeric material to an antimicrobial composition, the method including:

i) melting the polymeric material at temperatures up to about 400° C. to form a molten polymeric material;

ii) adding an antimicrobial compound to the molten polymeric material to form a mixture of the compound embedded in the polymeric material, wherein the compound comprises at least one quaternary ammonium group, at least one hydrocarbon chain comprising a minimum of 10 carbon atoms and a maximum of 24 carbon atoms, and one or more anions to balance the charge of the quaternary ammonium groups; and iii) cooling the mixture until it solidifies.

DETAILED DESCRIPTION

The invention relates to novel antimicrobial compositions consisting of a polymeric material and, embedded therein, an antimicrobial compound.

Any polymeric material that is solid at room temperature, and that is molten and stable at temperatures up to about 400° C. may be used in the invention. Preferably, the polymeric material is stable at temperatures up to about 500® F. when molten. Examples of polymeric materials include, but are not limited to, polyvinyl chloride, polyester, polyethylene, polypropylene, polystyrene, polymethacrylate, polyacrylate, polyacrylamide, nylon, and rayon. Examples of polyester include, but are not limited to polyethylene terephthalate, and poly-1,4-cyclohexylenedimethylene terephthalate. Other polymeric materials include natural and synthetic rubber.

The antimicrobial compound includes at least one quaternary ammonium group that comprises at least one hydrocarbon chain comprising a minimum of 10 carbon atoms and a maximum of 24 carbon atoms, and one or more anions to balance the charge of the quaternary ammonium groups.

The quaternary ammonium group can be part of a carbocyclic chain. The chain can be linear or branched. For example, the quaternary ammonium group that is part of a carbocyclic chain may comprise a dimethylammonium, diethylammonium, trimethylammonium, or triethylammonium group. Examples include hexadecyltrimethylammonium, octadecyltriethylammonium, di-dodecyldimethylammonium, di-propyldecyldiethylammonium (e.g., 5,6-di-n-propyldecyldiethylammonium), and di-heptadecyldipropylammonium.

An example of an acyclic compound containing one nitrogen atom is $(Y^3)_p\text{—}N^+\text{—}(Y^1\text{—}R^1)_r$, wherein p and r represents integers from 1-3 such that p+r=4. $Y^3$ represents a hydrocarbon group with a minimum of one carbon atom and a maximum of six carbon atoms. $Y^1$ represents a hydrocarbon chain comprising a minimum of 10 carbon atoms and a maximum of 24 carbon atoms. $R^1$ independently represent H, halo, or $OR^3$. Halo represents fluoro, chloro, bromo, or iodo. $R^3$ represents H or $R^4$. $R^4$ represents —$C(O)R^5$ or $R^6$. $R^5$ represents H or a hydrocarbon group, and $R^6$ represents a hydrocarbon group containing a minimum of one carbon atom and a maximum of four carbon atoms.

In this specification, a distinction is made between hydrocarbon groups and hydrocarbon chains. A hydrocarbon group is bonded at only one end to another chemical moiety. A hydrocarbon chain is bonded independently at each end to another chemical moiety, e.g., to a group, or to an atom.

The carbon atoms of a group or chain can all be saturated, or can all be unsaturated. Alternatively, a chain can comprise a mixture of saturated and unsaturated carbon atoms. The unsaturated hydrocarbon chains contain one or more double and/or triple bonds.

Some examples of saturated $C_{10}$-$C_{24}$ hydrocarbon chains include decyl, dodecyl, tetradecyl, hexadecyl, and octadecyl chains. Some examples of unsaturated $C_{10}$-$C_{24}$ hydrocarbon chains include oleyl, linoleyl, and linolenyl, especially cis-oleyl, cis, cis-linoleyl, and cis, cis, cis-linolenyl chains.

Examples of acyclic compounds containing two nitrogen atoms are shown below.

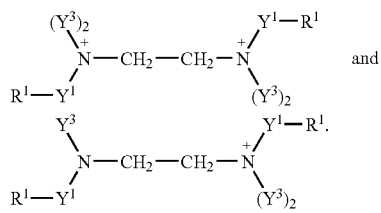

$Y^1$, $R^1$, and $Y^3$ are as described above.

The quaternary ammonium group may be part of a ring, such as a five or six member ring. The ring can be unfused or can be part of a fused ring system that contains one or two additional fused rings. The ring or fused ring system can be unsubstituted or substituted with one or more lower alkyl, halo, hydroxy, lower alkoxy, amino, lower alkylamino, or di-lower alkylamino or nitro groups. Any of the rings may be aromatic or non-aromatic.

Examples of five or six member rings in an unfused ring system include, but are not limited to, pyridinium, pyrrolium, piperidinium, pyrrolidinium, or di-piperazinium cation. Examples of five or six member rings in a fused ring system include, but are not limited to, indolinium, quinolinium, or isoquinolinium cation.

An example of a cyclic compound containing one nitrogen atom is

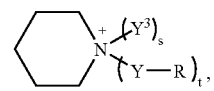

wherein s independently represents 0 or 1 and t independently represents 1 or 2 such that s+t=2.

Examples of cyclic compounds containing two nitrogen atoms are shown below.

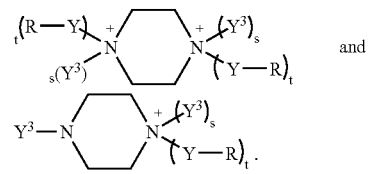

Y represents a hydrocarbon chain comprising a minimum of 10 carbon atoms and a maximum of 24 carbon atoms. $Y^3$ is as described above. R represents H, halo, or $OR^3$. $R^3$ is as described above.

Preferably, the quaternary ammonium group is part of a bridged ring system, such as 1-azonia-4-azabicyclo[2.2.2] octane (II) or 1,4-diazoniabicyclo[2.2.2]octane (III), shown below.

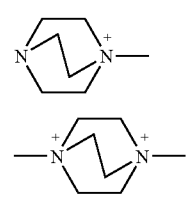

Additionally, the antimicrobial compound contains one or more anions to balance the charge of the quaternary ammonium groups. The anion may be singly charged, doubly charged, or triply charged. Some examples of anions include monovalent anions such as halides (e.g., $F^-$, $Cl^-$, $Br^-$, and $I^-$), $OH^-$, $NO_3^-$, and $H^-$; more preferably halides and $OH^-$; divalent anions such as $S^{-2}$, $CO_3^{-2}$, and $SO_4^{-2}$; and trivalent anions such as $PO_4^{-3}$ and $PO_3^{-3}$.

The letters $aB^{-c}$ represent the number and identity of anions necessary to maintain a charge-neutral compound. B represents any anion having a valence (c) of 1-3.

The letter a represents an integer such that the overall charge of the compound is neutral. For example, when the compound contains a divalent cation and B is Cl⁻, then a is 2 and c is 1. In another example, when the compound contains a divalent cation and B is S⁻², then a is 1 and c is 2.

In a preferred embodiment, the antimicrobial compound is represented by formula (I):

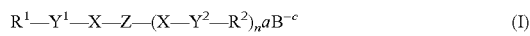

$$R^1-Y^1-X-Z-(X-Y^2-R^2)_n a B^{-c} \qquad (I)$$

Z represents a modified polyol having more than one primary hydroxyl group in its unmodified state wherein at least two of the primary hydroxyl groups have been replaced by $R^1-Y^1-X$ or $R^2-Y^2-X$ groups. The unmodified polyol can be any molecule having more than one primary hydroxyl group. The unmodified polyol may, for example, be an alkane polyol, a polyether, a carbohydrate, or a protein.

An alkane polyol of the present invention is an alkane with a minimum of two carbon atoms and a maximum of twelve carbon atoms, and at least two primary hydroxyl groups. Some examples of alkane polyols include glycerol; mannitol; ethylene glycol; 1,5-pentanediol; 1,2,3,4,5,6,7,8-octaneoctol; 1,6,12-dodecanetriol; and 3-methanolyl-1,6-hexanehexol.

The unmodified polyol can be a polyether. In this specification, polyether refers to molecules having at least two primary hydroxyl groups and having a minimum of one, and a maximum of about 10,000, preferably about 1,000, more preferably about 100, and most preferably about 10 ether groups. Some examples of polyethers include polyethylene glycol and polypropylene glycol.

Carbohydrates include saccharides, e.g., monosaccharides, oligosaccharides, and polysaccharides. The minimum number of saccharide units in an oligosaccharide is two. The maximum number of saccharide units in an oligosaccharide is typically twelve, preferably ten.

Polysaccharides have more than twelve saccharide units, and may have up to several thousand units, e.g. up to a maximum of about 10,000. In this specification, polysaccharides refer to polymers of (+)-glucose, and include cellulose, starch and glycogen. The saccharides can be in either the D or L configuration. Saccharide units can be either aldoses or ketoses.

The number of carbons in a saccharide unit can be from three carbons to about six carbons. An example of a three carbon sugar is glyceraldehyde. Examples of four carbon sugars include erythrose and threose. Examples of five carbon sugars include ribose, arabinose, xylose and lyxose. Examples of six carbon sugars include allose, altrose, glucose, mannose, gulose, idose, galactose and talose. All of these saccharides further include the corresponding 2'-deoxy derivatives.

The polyol can be a polyamino acid having at least two amino acids with primary hydroxyl groups. Polyamino acids include oligopeptides and proteins. An oligopeptide has two to twelve amino acid residues. Typically, proteins have more than twelve amino acid residues and up to about 1,000 amino acid residues.

The letter X in formula I represents 1,4-diazoniabicyclo[2.2.2]octane.

$Y^1$ and $Y^2$ independently represent hydrocarbon chains comprising a minimum of 10 carbon atoms and a maximum of 24 carbon atoms. Preferably, $Y^1$ and $Y^2$ represent a mixture of hydrocarbon chains.

Preferred chain lengths for $Y^1$ and $Y^2$ are 12, 14, 16, or 18 carbon atoms. In one illustrative embodiment, the mixture of hydrocarbon chains comprises a chain having 12 carbon atoms and a chain having 16 carbon atoms. For example, at least 25% of the hydrocarbon chains may have 12 carbon atoms and at least 25% of the hydrocarbon chains may have 16 carbon atoms. In another example, at least 75% of the hydrocarbon chains may have 12 carbon atoms or 16 carbon atoms. Likewise, at least 90% of the hydrocarbon chains may have 12 carbon atoms or 16 carbon atoms.

$R^1$ and $R^2$ independently represent H, halo, or $OR^3$. Halo represents fluoro, chloro, bromo, or iodo. $R^3$ represents H or $R^4$. $R^4$ represents $-C(O)R^5$ or $R^6$. $R^5$ represents H or a hydrocarbon group, and $R^6$ represents a hydrocarbon group containing a minimum of one carbon atom and a maximum of four carbon atoms.

The letter n in formula I represents the number of hydroxyl groups that have been replaced by $R^1-Y^1-X$ or $R^2-Y^2-X$, and may be any number greater than zero and up to m−1 wherein m represents the number of primary hydroxyl groups in the unmodified polyol, Z. The minimum value for m is two, preferably four, and more preferably six. The maximum number for m depends upon the type of polyol.

Carbohydrates can contain several thousand saccharide units. Each saccharide unit typically contains one primary hydroxyl group. Typically, for a carbohydrate, m should not be greater than 10,000.

Proteins may contain up to 1,000 amino acid residues and sometimes more. A typical protein contains about 300 amino acid residues. Of the twenty naturally occurring amino acids, only serine contains a primary hydroxyl group. Typically, m is not greater than 200 for a protein.

Preferably, alkane polyols of the present invention contain a minimum of two carbon atoms and a maximum of twelve carbon atoms, and at least two primary hydroxyl groups. Typically, m is not greater than eight for an alkane polyol of the present invention.

For example, when Z is 2,3-hydroxymethyl-1,4-butanediol, the alkane polyol contains four primary hydroxyl groups. The value of m is four and n may be any number up to three. An antimicrobial composition for 2,3-hydroxymethyl-1,4-butanediol may, for instance, have a value for n of two.

It is not necessary to activate all of the available primary hydroxyl sites present on the surface of a material. For example, less than about 10% of the available hydroxyl groups on a surface may be activated to subsequently provide sufficient antimicrobial activity. Preferably, about 25% of the available hydroxyl groups may be activated, more preferably about 50%, and most preferably about 75% of the available hydroxyl groups may be activated.

For example, when Z is a carbohydrate comprising 2,000 glucose units, m is 2,000, and n may be any number up to 1,999. An antimicrobial composition for a 2,000 unit carbohydrate may, for instance, have a value for n of 1,500.

In another example, when Z is a protein comprising 300 amino acid residues, fifteen of which are serine, m is fifteen, and n may be any number up to fourteen. An antimicrobial composition for a 300 residue protein may, for instance, have a value for n of seven.

The letters a, B, and c are as described above. In formula I, in order to maintain a charge neutral compound, a×c=2n+2.

Substitution of Hydroxyl Groups

Hydroxyl groups in the unmodified polyols useful in synthesizing compounds of the invention can be activated for substitution by a tertiary amine to form any of the quaternary ammonium groups described above. Some suitable tertiary amines include $Y-N(CH_3)_3$ or $Y-N(CH_3)_2-Y$ wherein Y represents $Y^1$, $Y^2$, or $Y^3$, 1,4-diazabicyclo[2.2.2]octane, or 1-azonia-4-azabicyclo[2.2.2]octane.

Activation of hydroxyl groups may be accomplished by methods known in the art. Suitable methods include, for example, converting the hydroxyl groups to electrophilic leaving groups. Suitable electrophilic leaving groups include, for example, a halo group or an active ester group.

Some suitable halo groups include chloro and bromo. Hydroxyl groups may, for example, be converted to chloro or bromo groups by treatment with thionyl chloride or phosphorus tribromide, respectively.

Suitable ester leaving groups include sulfonic acid esters. Hydroxyl groups may be converted to sulfonic acid esters by treating the hydroxyl groups with a suitable reagent, such as sufonyl chloride, in a suitable medium. Suitable sulfonyl chlorides include, for example, benzenesulfonyl chloride, p-toluenesulfonyl chloride, and methanesulfonyl chloride. Suitable media for the reaction include, but are not limited to, pyridine, hexane, heptane, ether, toluene, ethyl acetate, and mixtures thereof.

The amount of the reagents mentioned above, the volume of suitable media, and other reaction conditions are known to those in the art.

The activated polyols are then treated with an appropriate tertiary amine under conditions that cause the leaving groups to be replaced by a nitrogen atom of the tertiary amine. Such conditions are well known in the art.

The resulting polyols are the modified polyols of the invention.

Antimicrobial Activity

The embedded polymeric materials according to the invention demonstrate antimicrobial properties. In this specification, antimicrobial properties refer to the ability to resist growth of single cell organisms, e.g., bacteria, fungi, algae, and yeast, as well as mold.

The bacteria include both gram positive and gram negative bacteria. Some examples of Gram positive bacteria include, for example, *Bacillus cereus, Micrococcus luteus*, and *Staphylococcus aureus*. Some examples of Gram negative bacteria include, for example, *Escherichia coli, Enterobacter aerogenes, Enterobacter cloacae*, and *Proteus vulgaris*. Strains of yeast include, for example, *Saccharomyces cerevisiae*.

A particular advantage of such action is the lack of consumption of the antimicrobial agent. Moreover, the antimicrobial activity is non-specific and non-metabolic. Therefore, the danger of encouraging resistant strains of microbes is reduced.

Antimicrobial Products

The polymeric compositions of the invention may be used to make numerous products that benefit from having antimicrobial activity. Such antimicrobial products may be embedded in any useful surface that can benefit from antimicrobial activity. Some examples of useful products include working surfaces, such as those in vehicles, public and private facilities, places of commerce, homes, factories, offices and other establishments; and including walls, floors, furniture, and fixtures; as well as HVAC, plumbing and other equipment; and in textiles and fabrics, building products, cellulose and paper goods; and also in medical articles and personal articles, including but not limited to those for protection and treatment, for personal care, and for various articles of wear, and for other uses.

More specific examples of products made from polymeric material in which antimicrobial compounds may be embedded include, but are not limited to, furniture, Petri dishes, clothing, countertops, condoms, tents, shower curtains, brushes, toys, flooring covers, gymnastic equipment (including mats), hot tubs, food and beverage containers, plastic bags, cutting boards, toilet seats, animal carriers, litter boxes, door mats, pool liners, adhesive bandages, telephones, keyboards, shoes, and insoles.

In a preferred embodiment, the antimicrobial compound is embedded in fibers, yarns, or fabric. Preferably, the fiber, yarn, or fabric is embedded in web form. The fibers, yarns, and fabrics may be natural, synthetic, or blends thereof. Some examples of natural fibers, yarns, and fabrics include cotton, silk and wool or blends thereof. Some examples of synthetic fibers, yarns, and fabrics include polyolefin, rayon, nylon, acrylate, and methacrylate or blends thereof. The substrate may be a woven, knit, or engineered "web," i.e., a formed non-woven.

Method of Embedding

The antimicrobial compound may be embedded in the polymeric material by methods known in the art. In one embodiment, the invention is related to a method of making an antimicrobial composition by providing a polymeric material, such as those described above, that is in a solid state at room temperature; melting the polymeric material at temperatures up to about 400° C. to form a molten polymeric material; adding an antimicrobial compound described above to the molten polymeric material to form a mixture of the compound embedded in the polymeric material; and cooling the mixture until it solidifies. Preferably, the polymeric material is heated up to temperatures of about 500° F. The antimicrobial compound may be added to the molten polymeric material by any suitable method. For example, the antimicrobial compound may be applied to the surface of the polymeric material before or after melting the polymeric material, or by injecting the antimicrobial compound into the molten polymeric material. All other steps are as described above.

The polymeric material may be heated by any known method. Preferred methods include convection heating, microwave heating, and contact heating.

The polymeric material and embedded compound are as described above. A polymeric material is molten when it is sufficiently fluid that a chemical compound can be dispersed within it.

The compound may be evenly dispersed within the polymeric material. Alternatively, the compound may be concentrated within the area surrounding the surface of the polymeric material.

For example, the heating of the solid polymeric material may be controlled, e.g. in an oven, so that only up to 5%, 10%, 25%, or 50% of the outer portion of the material becomes molten. Then the antimicrobial compound is added to the molten material. Once, the polymeric material is cooled and solidified, the surface of the material, and the area surrounding the surface of the material, will be antimicrobial.

The antimicrobial compound may be applied to the polymeric material before or after it is made molten by any method known in the art. For example, the antimicrobial compound may be in a solution that is applied to the polymeric material. The solution may be applied to the polymeric material by known methods such as coating, spraying, paddling, application by laundry equipment, exhausting on dyeing machinery, or dipping.

The antimicrobial solution may optionally include a binder system or other auxiliary chemistry to enhance the value or performance characteristics of the treated product. Examples of binder systems include acrylics and urethanes. Examples of auxiliary chemistry include compounds utilized to enhance the durability to light, washing, or post-treatment of the product; and compounds utilized to impart water repellency, flame resistance and fireproofing, anti-static, and other characteristics to the product. Such compound may include silica, carbon, and fiberglass.

The antimicrobial compound may be applied to the polymeric material at any time during the fabric forming process by methods known in the art. In particular, the antimicrobial compound may be introduced to the yarn, i.e., polymeric material when it is in pellet form or during the extrusion process. The antimicrobial compound may also be introduced as the web is being form from the yarn or after the fabric is fully formed.

In one embodiment, the antimicrobial compound is introduced into fibers, yarn, or fabric during the fabric forming process by methods known in the art. In the process described in U.S. Pat. No. 4,376,802 for example, yarn is treated with a stiffener-containing fiber finish, twisted into cord, and then weaved to make a fabric utilizing the treated cord. The woven fabric is exposed for an effective time period, preferably 1 to 1.5 minutes, to a temperature which causes the composition to stiffen the fabric without damaging the fiber. The temperature is preferably at least about 171° C. (340° F.) to a maximum of about 240° C. (464° F.). The fabric forming process described at Col. 1, line 31 to col. 3, line 12 of U.S. Pat. No. 4,376,802 is incorporated herein by reference.

An antimicrobial composition of the present invention may be applied during the fabric forming process described in U.S. Pat. No. 4,376,802, either immediately before or after the heating step. The fabric must be heated to a temperature high enough to melt the polymeric fibers and create a molten polymeric material. The fabric is then cooled, so that the polymeric material solidifies.

The antimicrobial compound may also be introduced to fabric or webbing during a dyeing process. For example, the antimicrobial may be added during the Thermasol Process described in U.S. Pat. No. 4,376,802. The steps of the Thermasol Process are listed at col. 2, line 54 to col. 3, line 12 in U.S. Pat. No. 4,376,802 as including:

1) Pad on disperse syestuffs at temperatures up to 140° F. (60° C.).
2) Pass dye-impregnated webbing through infra-red pre-dryer.
3) Dry in air drier at 230°-250° F. (110°-130° C.).
4) Pass through Thermasol oven for 2 minutes at 374°-430° F. (190°-221° C.).
5) Pad on 2 gpl caustic soda and 2 gpl sodium hydrosulfite 80° F. (27° C.).
6) Steam 2-8 minutes.
7) Wash with synthetic detergent at 205°-212° F. (96°-100° C.) 2 or more boxes.
8) Hot water rinse 205°-212° F.
9) Rinse in a cold solution of 5 gpl acetic acid (56%).
10) Dry in hot air oven and/or steam cans 250° F. (130° C.).

In the Thermasol Process, the antimicrobial composition of the present invention may be added immediately before or after step 4) while the fabric or webbing is at a temperature of 374°-430° F.

The value of the end product is enhanced by having embedded antibiotic molecules. In a preferred embodiment, the end product is a fabric or textile. For example, the end product may be a woven, non-woven, knit, or blend thereof. The end product may include synthetic fibers, natural fibers, or blends thereof For example, the end product may be clothing, such as a shirt, pants, skirt, jacket, or coat, such as a laboratory coat, made of a cotton/polyester blend. In another embodiment, the product may include thermoplastic yarns, natural yarns, or combinations thereof.

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a first group of parameters, e.g., a, b, c, d, and e, may be combined with the members of a second group of parameters, e.g., A, B, C, D, and E. Any member of the first group or of a sub-group thereof may be combined with any member of the second group or of a sub-group thereof to form additional groups, i.e., b with C; a and c with B, D, and E, etc.

For example, in the present invention, groups of various parameters are defined (e.g. $R^1$, $R^2$, $R^3$, $R^4$, $R^5$, $R^6$, $Y^1$, and $Y^2$). Each group contains multiple members. For example, $R^2$ represents H, halo, or $OR^3$. Each member may be combined with each other member to form additional sub-groups, e.g., H and halo, H and $OR^3$, and halo and $OR^3$.

The instant invention further contemplates embodiments in which each element listed under one group may be combined with each and every element listed under any other group. For example, $Y^1$ and $Y^2$ are identified above as independently representing a hydrocarbon chain comprising a minimum of 10 carbon atoms and a maximum of 24 carbon atoms. $R^1$ and $R^2$ are identified above as independently representing H, halo, or $OR^3$. Each element of $Y^1$ and $Y^2$ (a hydrocarbon chain comprising a minimum of 10 carbon atoms and a maximum of 24 carbon atoms) can be combined with each and every element of $R^1$ and $R^2$ (H, halo, or $OR^3$). For example, in one embodiment, $Y^1$ may be a 16 carbon atom chain; $Y^2$ may be a 12 carbon atom chain; $R^1$ may be Cl; and $R^2$ may be H. Alternatively, $Y^1$ may be a 18 carbon atom chain; $Y^2$ may be a 24 carbon atom chain; $R^1$ may be $OR^3$; and $R^2$ may be Br, etc. Similarly, a third group is $R^3$, in which the elements are defined as H or $R^4$. Each of the above embodiments may be combined with each and every element of $R^3$. For example, in the embodiment wherein $Y^1$ is a 14 carbon atom chain; $Y^2$ is a 20 carbon atom chain; $R^1$ is H; and $R^2$ is $OR^3$, $R^3$ may be H (or any other chemical moiety within the element of $R^3$).

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

A list following the word "comprising" is inclusive or open-ended, i.e., the list may or may not include additional unrecited elements. A list following the words "consisting of" is exclusive or closed ended, i.e., the list excludes any element not specified in the list.

All numbers in the specification are approximate unless indicated otherwise.

The method of treating a condition, disorder or disease with a chemical compound or a chemical composition includes the use of the chemical compound or chemical composition in the manufacture of a medicament for the treatment of the condition, disorder or disease. A compound or a group of compounds said to be effective in treating a condition, disorder or disease includes the compound or group of compounds for use in treating the condition, disorder or disease.

EXAMPLES

Example 1

Application of Modified DABCO Detergent to Polyester Fabric

The agent, bis-1',3'-(1-hexadecyl)-1,4-diazoniabicyclo[2.2.2]octane-2'-propanol tetrachloride, was placed in an aqueous solution (10% of agent by weight) and the polyester to be treated was saturated with this solution. The polyester fabric was pressed under a roller to remove excess liquid and then heated at 400° F. for 30 sec. to cause dissolution in the polyester material, and then cooled to ambient temperature.

Example 2

Preparation of DABCO in PVC

To a preparation of PVC prepared for finishing and heated to 350° F. is added the agent bis-1',3'-(1-hexadecyl)-1,4-diazoniabicyclo[2.2.2]octane-2'-propanol tetrachloride in an amount of 10 g/square meter of finished surface. After pressing and cooling samples the surface is antimicrobial.

Example 3

Antimicrobial Assessment of Embedded Polyesters

Three types of polyester fabric are embedded with bis-1',3'-(1-hexadecyl)-1,4-diazoniabicyclo[2.2.2]octane-2'-propanol tetrachloride. Three polyester samples supplied by Gar are tested—a) "144×90", b) "Spandex" which is 5% lycra with polyester, and c) "Darlington." Each fabric sample is placed onto a mineral salts agar medium and then inoculated with either *Staphylococus aureus* or *Escherichia coli*. The inoculated specimen is then incubated at 28° C. for 28 days, in order to allow adequate time for bacterial growth. The fabric samples show a complete kill of both *Staphylococus aureus* and *Escherichia coli*.

We claim:

1. A solid antimicrobial composition consisting of:
   a) a polymeric material that is solid at room temperature and molten at elevated temperatures and, embedded therein,
   b) a compound represented by formula (I):

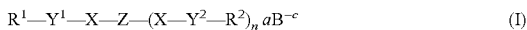
$$R^1-Y^1-X-Z-(X-Y^2-R^2)_n aB^{-c} \qquad (I)$$

wherein:
Z represents a modified polyol having more than one primary hydroxyl group in its unmodified state, wherein at least two of the primary hydroxyl groups have been replaced by $R^1-Y^1-X$ or $R^2-Y^2-X$ groups;
X represents 1,4-diazoniabicyclo[2.2.2]octane;
$Y^1$ and $Y^2$ independently represent hydrocarbon chains comprising a minimum of 10 carbon atoms and a maximum of 24 carbon atoms;
$R^1$ and $R^2$ independently represent H, halo, or $OR^3$;
$R^3$ represents H or $R^4$;
$R^4$ represents —C(O)$R^5$ or $R^6$;
$R^5$ represents H or a hydrocarbon group comprising a minimum of 1 carbon atom and a maximum of 4 carbon atoms;
$R^6$ represents a hydrocarbon group comprising a minimum of 1 carbon atom and a maximum of 4 carbon atoms;
n represents a number up to m−1 wherein m represents the number of primary hydroxyl groups in the unmodified polyol;
B represents an anion;
a represents an integer; and c represents 1−3; wherein a×c=2n+2.

2. A solid antimicrobial composition according to claim 1, wherein the polymeric material is selected from the group consisting of polyvinyl chloride, a polyester, polyethylene, polypropylene, polystyrene, polymethacrylate, polyacrylate, polyacrylamide, nylon, and rayon.

3. A solid antimicrobial composition according to claim 2, wherein the polyester is selected from the group consisting of polyethylene terephthalate, and poly-1,4-cyclohexylenedimethylene terephthalate.

4. A solid antimicrobial composition according to claim 1, wherein the polymeric material is natural or synthetic rubber.

5. A solid antimicrobial composition according to claim 1, wherein the polyol is an alkane polyol.

6. A solid antimicrobial composition according to claim 5, wherein the alkane polyol is glycerol, mannitol, or ethylene glycol.

7. A solid antimicrobial composition according to claim 1, wherein the polyol is a polyether.

8. A solid antimicrobial composition according to claim 7, wherein the polyether is polyethylene glycol or polypropylene glycol.

9. A solid antimicrobial composition according to claim 1, wherein the polyol is a carbohydrate.

10. A solid antimicrobial composition according to claim 1, wherein the polyol is a protein.

11. A solid antimicrobial composition according to claim 1, wherein $Y^1$ and $Y^2$ comprise a hydrocarbon chain having 12, 14, 16, or 18 carbon atoms.

12. A solid antimicrobial composition according to claim 1, wherein $Y^1$ and $Y^2$ represents a mixture of hydrocarbon chains.

13. A solid antimicrobial composition according to claim 1, wherein the mixture of hydrocarbon chains comprises a hydrocarbon chain having 12 carbon atoms and a hydrocarbon chain having 16 carbon atoms.

14. A solid antimicrobial composition according to claim 1, wherein at least 25% of the hydrocarbon chains have 12 carbon atoms and at least 25% of the hydrocarbon chains have 16 carbon atoms.

15. A solid antimicrobial composition according to claim 1, wherein at least 75% of the hydrocarbon chains have 12 carbon atoms or 16 carbon atoms.

16. A solid antimicrobial composition according to claim 1, wherein at least 90% of the hydrocarbon chains have 12 carbon atoms or 16 carbon atoms.

17. A solid antimicrobial composition according to claim 1, wherein $R^1$ and $R^2$ independently represent H, Cl, or OH.

18. A solid antimicrobial composition according to claim 17, wherein $R^1$ and $R^2$ represent H.

19. A method of making a solid antimicrobial composition, the method comprising:
   i) providing a polymeric material that is in a solid state at room temperature;
   ii) melting the polymeric material at temperatures up to about 400° C. to form a molten polymeric material;
   iii) adding an antimicrobial compound to the molten polymeric material to form a mixture of the compound embedded in the polymeric material; and
   iv) cooling the mixture until it solidifies, wherein the solid antimicrobial composition consists of the polymeric material that is solid at room temperature and molten at elevated temperatures and, embedded therein, is the compound, wherein the compound is represented by formula (I):

$$R^1\text{—}Y^1\text{—}X\text{—}Z\text{—}(X\text{—}Y^2\text{—}R^2)_n\, aB^{-c} \qquad (I)$$

wherein:

Z represents a modified polyol having more than one primary hydroxyl group in its unmodified state, wherein at least two of the primary hydroxyl groups have been replaced by $R^1\text{—}Y^1\text{—}X$ or $R^2\text{—}Y^2\text{—}X$ groups;

X represents 1,4-diazoniabicyclo[2.2.2]octane;

$Y^1$ and $Y^2$ independently represent hydrocarbon chains comprising a minimum of 10 carbon atoms and a maximum of 24 carbon atoms;

$R^1$ and $R^2$ independently represent H, halo, or $OR^3$;

$R^3$ represents H or $R^4$;

$R^4$ represents —$C(O)R^5$ or $R^6$;

$R^5$ represents H or a hydrocarbon group comprising a minimum of 1 carbon atom and a maximum of 4 carbon atoms;

$R^6$ represents a hydrocarbon group comprising a minimum of 1 carbon atom and a maximum of 4 carbon atoms;

n represents a number up to m−1 wherein m represents the number of primary hydroxyl groups in the unmodified polyol;

B represents an anion;

a represents an integer; and c represents 1–3; wherein a x c=2n+2.

20. A method according to claim 19, wherein the antimicrobial compound is applied to the surface of the polymeric material before heating the polymeric material to form a molten polymeric material.

21. A method according to claim 19, wherein the antimicrobial compound is applied to the surface the polymeric material after heating the polymeric material to form a molten polymeric material.

22. A method according to claim 19, wherein the antimicrobial compound is injected into the molten polymeric material.

23. A method according to claim 19, wherein the polymeric material is melted at temperatures up to about 500° F. to form a molten polymeric material.

24. A method of converting a polymeric material to a solid antimicrobial composition, the method comprising:

i) melting the polymeric material at temperatures up to about 400° C. to form a molten polymeric material;

ii) adding an antimicrobial compound to the molten polymeric material to form a mixture of the compound embedded in the polymeric material; and iii) cooling the mixture until it solidifies, wherein the solid antimicrobial composition consists of the polymeric material that is solid at room temperature and molten at elevated temperatures and, embedded therein, is the compound, wherein the compound is represented by formula (I):

$$R^1\text{—}Y^1\text{—}X\text{—}Z\text{—}(X\text{—}Y^2\text{—}R^2)_n\, aB^{-c} \qquad (I)$$

wherein:

Z represents a modified polyol having more than one primary hydroxyl group in its unmodified state, wherein at least two of the primary hydroxyl groups have been replaced by $R^1\text{—}Y^1\text{—}X$ or $R^2\text{—}Y^2\text{—}X$ groups;

X represents 1,4-diazoniabicyclo[2.2.2]octane;

$Y^1$ and $Y^2$ independently represent hydrocarbon chains comprising a minimum of 10 carbon atoms and a maximum of 24 carbon atoms;

$R^1$ and $R^2$ independently represent H, halo, or $OR^3$;

$R^3$ represents H or $R^4$;

$R^4$ represents —$C(O)R^5$ or $R^6$;

$R^5$ represents H or a hydrocarbon group comprising a minimum of 1 carbon atom and a maximum of 4 carbon atoms;

$R^6$ represents a hydrocarbon group comprising a minimum of 1 carbon atom and a maximum of 4 carbon atoms;

n represents a number up to m−1 wherein m represents the number of primary hydroxyl groups in the unmodified polyol;

B represents an anion;

a represents an integer; and c represents 1–3; wherein a x c=2n+2.

25. A method according to claim 24, wherein the antimicrobial compound is applied to the surface of the polymeric material before heating the polymeric material to form a molten polymeric material.

26. A method according to claim 24, wherein the antimicrobial compound is applied to the surface the polymeric material after heating the polymeric material to form a molten polymeric material.

27. A method according to claim 24, wherein the antimicrobial compound is injected into the molten polymeric material.

28. A method according to claim 24, wherein the polymeric material is melted at temperatures up to about 500° F. to form a molten polymeric material.

* * * * *

UNITED STATES PATENT AND TRADEMARK OFFICE
CERTIFICATE OF CORRECTION

PATENT NO. : 8,470,351 B2
APPLICATION NO. : 12/129805
DATED : June 25, 2013
INVENTOR(S) : Engel et al.

It is certified that error appears in the above-identified patent and that said Letters Patent is hereby corrected as shown below:

IN THE SPECIFICATION:

Column 3, line 4:

Now reads: "about 500®F. when"

Should read: -- about 500°F when --

Column 9, lines 65-66:

Now reads: "blends thereof For example,"

Should read: -- blends thereof. For example, --

Signed and Sealed this
Twentieth Day of August, 2013

Teresa Stanek Rea
*Acting Director of the United States Patent and Trademark Office*